United States Patent

Sham et al.

[11] Patent Number: 5,891,042
[45] Date of Patent: Apr. 6, 1999

[54] FITNESS MONITORING DEVICE HAVING AN ELECTRONIC PEDOMETER AND A WIRELESS HEART RATE MONITOR

[75] Inventors: Ka Yiu Sham, Great Falls, Va.; Philip Lim-Kong Wong, Northants, England

[73] Assignee: Acumen, Inc., Sterling, Va.

[21] Appl. No.: 926,035

[22] Filed: Sep. 9, 1997

[51] Int. Cl.⁶ .................................................. A61B 5/0205
[52] U.S. Cl. ................................................................ 600/483
[58] Field of Search ............................... 600/483, 503, 600/508, 509, 519, 520; 128/903

[56] References Cited

U.S. PATENT DOCUMENTS

| | | | |
|---|---|---|---|
| 4,367,752 | 1/1983 | Jimenez et al. | 600/519 |
| 5,335,664 | 8/1994 | Nagashima | 128/903 |
| 5,456,262 | 10/1995 | Birnbaum . | |
| 5,491,474 | 2/1996 | Suni et al. . | |
| 5,539,706 | 7/1996 | Takenaka et al. . | |

*Primary Examiner*—William E. Kamm
*Attorney, Agent, or Firm*—Evenson, McKeown, Edwards & Lenahan P.L.L.C.

[57] ABSTRACT

A fitness monitoring device includes an electronic pedometer which responds to a user's body motion at each step and a wireless heart rate monitor which is wirelessly coupled to the electronic pedometer. The wireless heart rate monitor provides a heart beat signal indicative of an exertion level of the user. A visual display is provided to display the pedometer functions and the heart rate signal. A microprocessor receives the pedometer output signal and the heart rate signal. The microprocessor is programmed to provide visual display data relating to the heart rate and pedometer functions.

9 Claims, 5 Drawing Sheets

FITNESS MONITORING DEVICE HAVING AN ELECTRONIC PEDOMETER AND A WIRELESS HEART RATE MONITOR

FIELD OF THE INVENTION

This invention relates to a fitness activity monitoring device and, more particularly, to a fitness activity monitoring device which monitors the heart rate of its user while providing pedometer functions.

BACKGROUND OF THE INVENTION

In order to measure the walking or jogging distance covered by a user, both mechanical and electronic pedometers have been developed. Typically, such pedometers are worn on the side of the user such as by being clipped to a belt or the waist line of the user's pants in the manner of a pager or the like. Other known pedometers are built into a wrist watch worn on the user's wrist. In general, the pedometer functions to record the distance covered by the user by responding to the user's body motion at each step. Pedometers include various features and functions such that they can be adapted to the personal stride of the user. The pedometer includes a display, such as an LCD or LED display, for displaying the distance covered, number of steps taken during the workout, stopwatch and clock features, etc.

In most cases, the known pedometers use a mechanical sensing device to respond to the user's body motion at each step. However, the use of the mechanical sensor is disadvantageous as it is more susceptible to breakage and inaccuracies.

Electronic pedometers are also known which include an electronic sensor circuit to respond to the user's body motion at each step or stride. These electronic pedometers are more reliable and less susceptible to breakage.

While the known pedometers provide useful information during a workout, they unfortunately do not provide the user with any indication as to the level of exertion being placed on the user's body. Thus, while specific performance limitations may be indicated, the pedometer cannot inform the user whether they are training to hard or to little. The user therefore needs some indication of the degree of physical effort actually exerted as measured by physiological signs. The use of physiological signs provides a more direct indication to guide the exercise than the information provided by the known pedometers such as the distance travelled, amount of time involved, or the physical work load.

In view of the above, heart rate monitors have been developed to allow a person to consistently engage in an appropriate quantity and quality of exercise by monitoring the cardiovascular system via the heart rate. In general, effective aerobic conditioning requires that one's heart rate is maintained at a proper level or "target zone" for at least fifteen minutes. Prior to the use of heart rate monitors, a person would have to interrupt the workout in order to manually check their heart rate before continuing or modifying the exertion level of their workout. Of course, the sudden interruption of a workout to check the heart rate is itself disadvantageous.

One known method of monitoring the heart rate uses electrodes attached to the user in the vicinity of the heart. Electrical signals detected by the electrodes are transmitted via conductors or wires to a processor which can compute the heart rate. These "wired" heart rate monitors present various problems in that the wires often interfere with an exercise workout, particularly during running or walking workouts. They are therefore not particularly suited to active exercising.

There have also been developed so-called "wireless" heart rate monitors which use a telemetric transmitter unit for wirelessly transmitting electrical signals detected by electrodes to a separate receiver device. One such telemetric transmitter unit is described in U.S. Pat. No. 5,491,474. It is also known to use wired or telemetric wireless heart rate monitors with stationary exercise devices such as a cycle ergometer as described, for example, in U.S. Pat. No. 5,456,262. The ergometer is used to simulate an exercise program. However, such combined devices restrict the user's exercise routines to stationary exercise units.

Pedometers have also been developed which incorporate pulse meters for sensing the user's heartbeat, such as in U.S. Pat. No. 5,539,706. In contrast to heart rate monitors which determine the heartbeat in beats per minute (bpm) based on electrical signals from the heart, the pulse meters calculate the heartbeat by sensing blood flow through the user's veins. Typically, pulse meters incorporate an infrared light sensor which is pressed against the user's fingertip or clipped against the user's ear. The infrared light sensor determines how fast the user's blood is pumping through their veins. Unfortunately, such pulse meters encounter problems in that if the user's finger is pressed too hard against the sensor, the blood flow will slow down. By contrast, if pressed too lightly against the sensor, then even the slightest movement of the user's fingertip can give erratic readings. Similarly, the ear-clip pulse meter models can also provide faulty readings due to poor circulation in the user's ears, or to sensor movements caused by the connecting wires which must dangle from the sensor. While the use of pulse meters is accurate when the user remains very still, they become unstable and inaccurate during a fitness routine. This therefore defeats the purpose of using the pulse meter to determine the user's heartbeat during exercise. Proper use of heart rate measurement requires that the user be aware of the heart rate during the exercise. As noted above, however, accurate readings with the pulse meters are accomplished by interrupting or slowing down the exercise routine, which has its own disadvantages notwithstanding the fact that the user's heart rate instantaneously lowers during a stoppage or slow down.

There is therefore needed a fitness monitoring device which can effectively provide the user with physiological information concerning their exercise level while at the same time providing empirical information with respect to the duration and extent of a workout.

SUMMARY OF THE INVENTION

These needs are met according to the present invention by providing a fitness monitoring device having an electronic pedometer and a wireless heart rate monitor. The present invention provides all of the functional features of a pedometer together with the advantageous features of a wireless heart rate monitor.

The fitness monitoring device according to the invention measures the actual electrical signal from the user's heart via a chest belt transmitter, such as a telemetric transmitter, which is placed on the user's skin next to the heart. The transmitter transmits the heart rate signal, or some variation thereof, to a processor in the electronic pedometer via a high frequency magnetic field in a wireless manner. The microprocessor in the electronic pedometer not only determines the user's heart rate, but also calculates a target zone heart rate based on the user's physical characteristics. Further, the microprocessor is programmed to calculate and display the pedometer functions such as the distance covered, number of steps taken, current speed, average speed, calories burned, etc.

Other objects, advantages and novel features of the present invention will become apparent from the following detailed description of the invention when considered in conjunction with the accompanying drawings.

BRIEF DESCRIPTION OF THE DRAWINGS

FIGS. 4 and 4a are a circuit diagram of the electronic pedometer used in the fitness monitoring device and an equivalent electrical circuit for the sensor, respectively, according to the present invention;

DETAILED DESCRIPTION OF THE DRAWINGS

Figure 1:
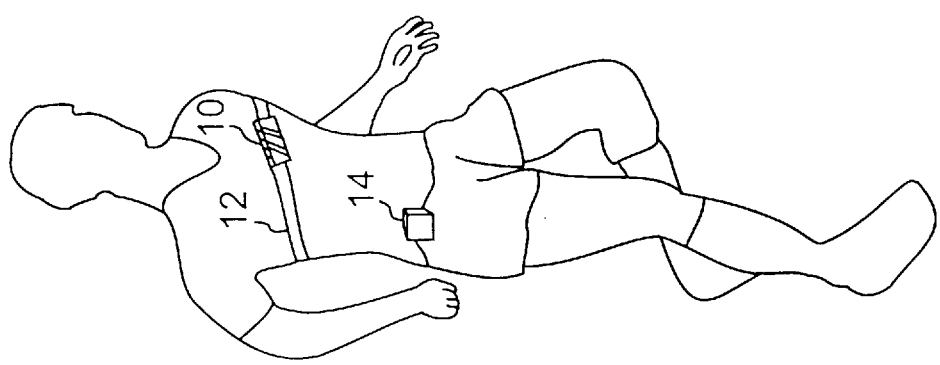
FIG. 1 is a schematic diagram of a jogger using the fitness monitoring device according to the present invention.

Referring to FIG. 1, a user is shown performing a running workout routine. The user has a wireless telemetric transmitter unit 10 arranged on the user's skin adjacent his heart. The telemetric transmitter unit 10 can be secured in this position via a belt strap 12. Further details regarding the belt strap and the manner in which the belt strap arranges the transmitter unit adjacent the heart are not necessary for an understanding of the present invention, although they are provided in copending application Ser. No. 08/577,015, filed Dec. 22, 1995, commonly assigned to the assignee of the present invention.

The user is also provided with a fitness monitoring device 14 which can, for example, be clipped to the user's waist band. Of course, the fitness monitoring device 14 can be secured to the user in other ways such as via a wrist watch-type arrangement or by simply being held by the user. As will be described in further detail below, the fitness monitoring device 14 includes an electronic pedometer integrated together with a wireless heart rate monitor. In this manner, no cumbersome lead lines must be provided between the telemetric transmitter unit 10 and the fitness monitoring device 14.

Figure 2:
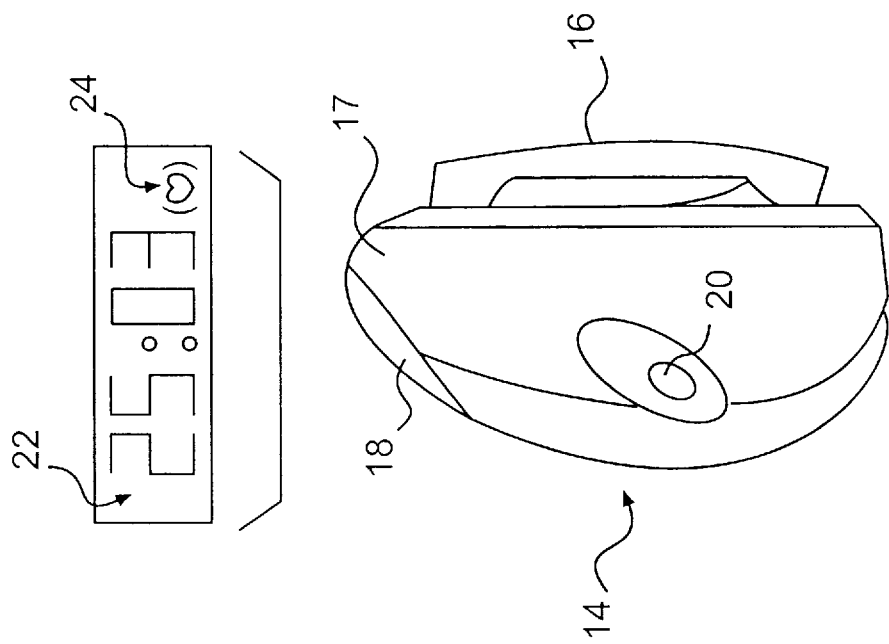
FIG. 2 is a side view of the fitness monitoring device according to the present invention, including a display which is viewed by the user.

Referring to FIG. 2, there is shown a side view of a fitness monitoring device 14. The fitness monitoring device 14 includes a belt clip 16 which allows the device 14 to be secured to the user's belt or waist band. Further, the fitness monitoring device 14 includes a display 18 and an operating element 20 incorporated into its housing 17. Of course, more than one operating element 20 can be provided in order to allow the user to make full use of the functional capabilities of the fitness monitoring device 14. The display 18 can be, for example, an LCD display which includes an alpha/numeric display portion 22 as well as a heart rate monitoring indicator icon 24. Other shapes and forms of the fitness monitoring device 14, its operating elements 20 and its display 18 can be provided based on the specific requirements of the design without departing from the spirit and scope of the present invention.

Figure 3:
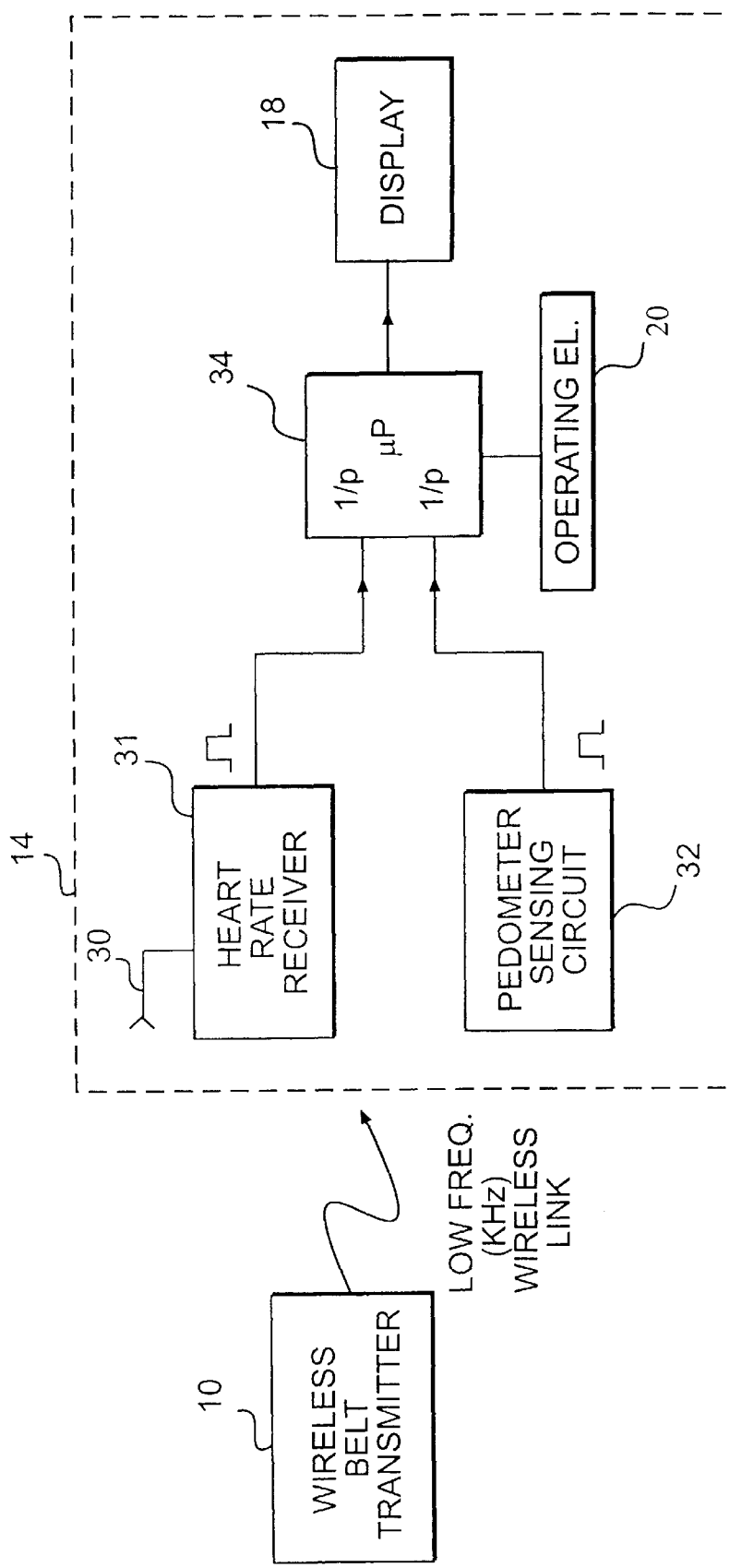
FIG. 3 is a circuit block diagram of the fitness monitoring device according to the present invention.

Referring to FIG. 3, there is shown a schematic block diagram of the fitness monitoring device 14. The fitness monitoring device 14 includes an antenna 30 which receives the telemetrically transmitted electrical signals from the telemetric transmitter 10. These signals are transmitted, for example, as a low frequency wireless link (in the kHz range). The signals from the antenna 30 are input to the heart rate receiver 31 Each time a heart beat pulse is received by the heart rate receiver 31, the heart rate receiver 31 will output a well defined pulse to the microprocessor 34. The microprocessor 34 then uses an averaging algorithm in order to calculate the heart rate. Similarly, an electronic pedometer circuit 32 provides input signals to the microprocessor 34. As the pedometer sensing circuit 32 outputs a pulse per step to the microprocessor 34, the microprocessor 34 will update and display the step counter. The microprocessor 34 further receives inputs from the operating elements 20. The display 18 is coupled to the microprocessor for displaying the processed results.

Figures 4A, 4B:
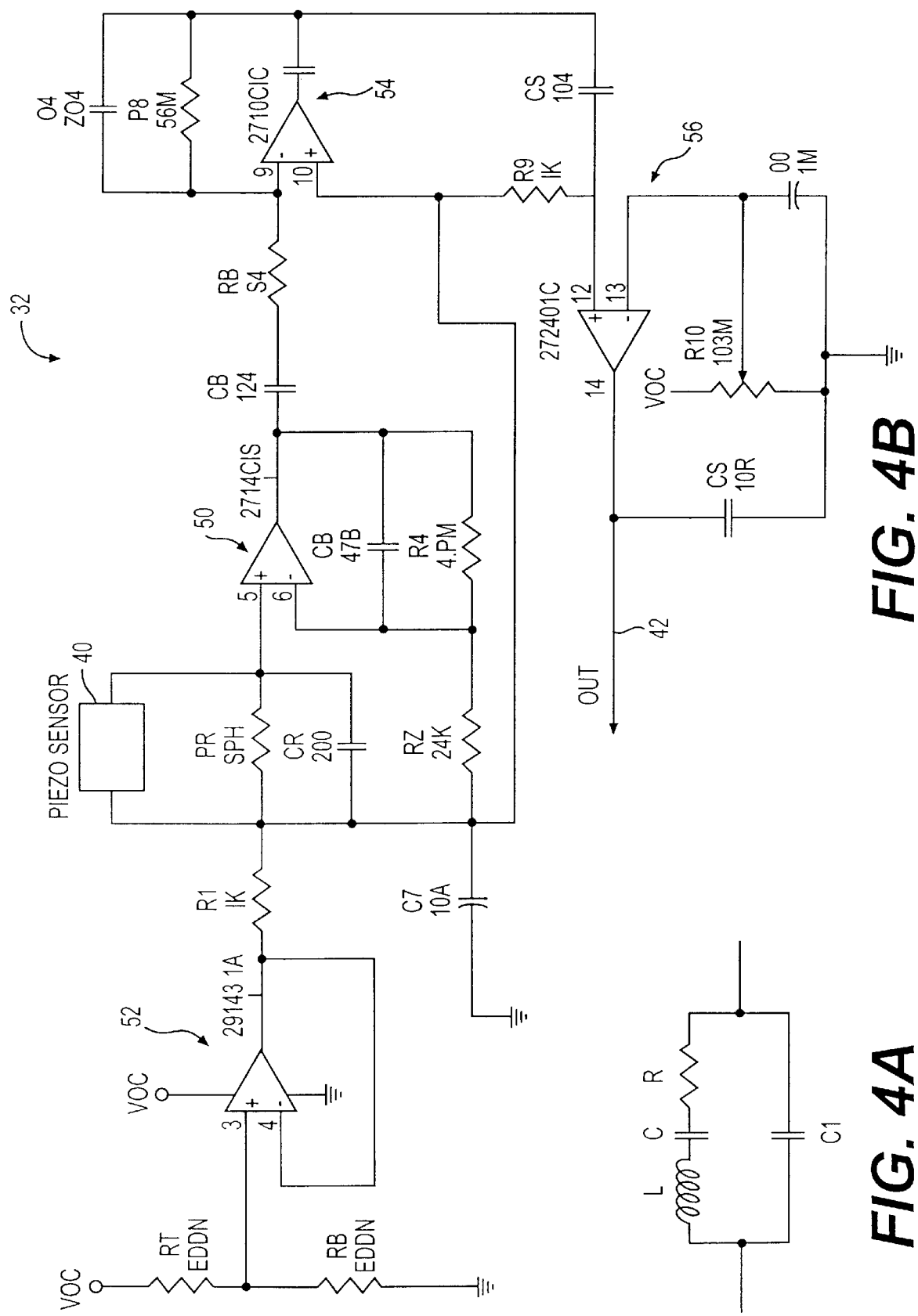

Referring to FIG. 4, there is shown a schematic circuit diagram of the electronic pedometer 32. The pedometer 32 makes use of a piezoelectric sensor 40 (quartz vibrator) for detecting the user's body motion at each step. At frequencies close to resonance, the operation of the quartz vibrator 40 can be modeled by the equivalent electrical circuit diagram of FIG. 4a (as far as the associated electrical circuits are concerned). In FIG. 4a, the inductance L represents the electrical equivalent of the vibrating mass of the piezo element 40. The capacitance C is the electrical equivalent of the mechanical compliance of the sensor 40. The resistance R represents the electrical equivalent of mechanical friction. In addition to the electrical equivalent L-R-C series resonance circuit for the mechanical quantities, there also is a parallel capacitance C1 which is the electrical capacitance of the quartz element between the terminal electrodes. It has been found that the ratio C1/C normally has a value of at least 125, such that C1>>C. Therefore, it is this capacitance C1, together with the amplification performed by operational amplifier 50 (IC1:B) that forms the vibration sensor. The operational amplifier circuit 52 (IC1:A) provides the voltage source to bias the sensor mid-point operating voltage. Operational amplifier circuit 54 (IC1:C) functions as a low-pass filter/integrator to remove high frequency signal components. Finally, the output operational amplifier circuit 56 (IC1:D) functions as a voltage comparator to generate a single pulse corresponding to a user's step. This pulse is fed into the microprocessor 34 (FIG. 3) for performing step counting.

Figure 5:
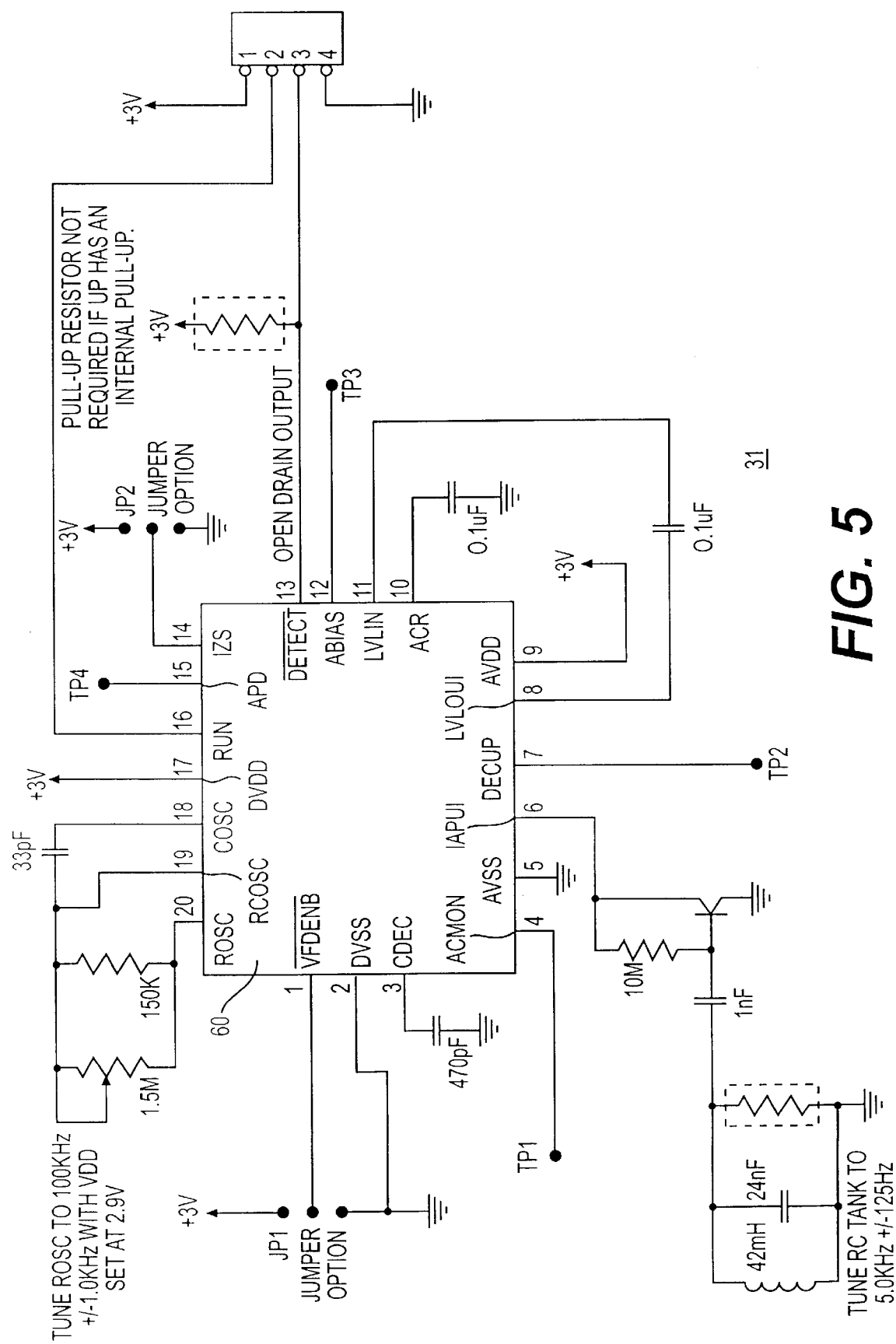
FIG. 5 is an electrical circuit diagram of a heart rate receiver.

Referring to FIG. 5, there is shown the circuit diagram for the heart rate receiver 31. The heart rate receiver makes use of a processor or hard wired circuit 60 in order to receive the low frequency signals from the wireless belt transmitter 10 and convert them into well-defined output pulses representative of the heart rate to the microprocessor 34. The heart rate receiver circuit shown in FIG. 5 is a conventionally known circuit.

Figure 6:
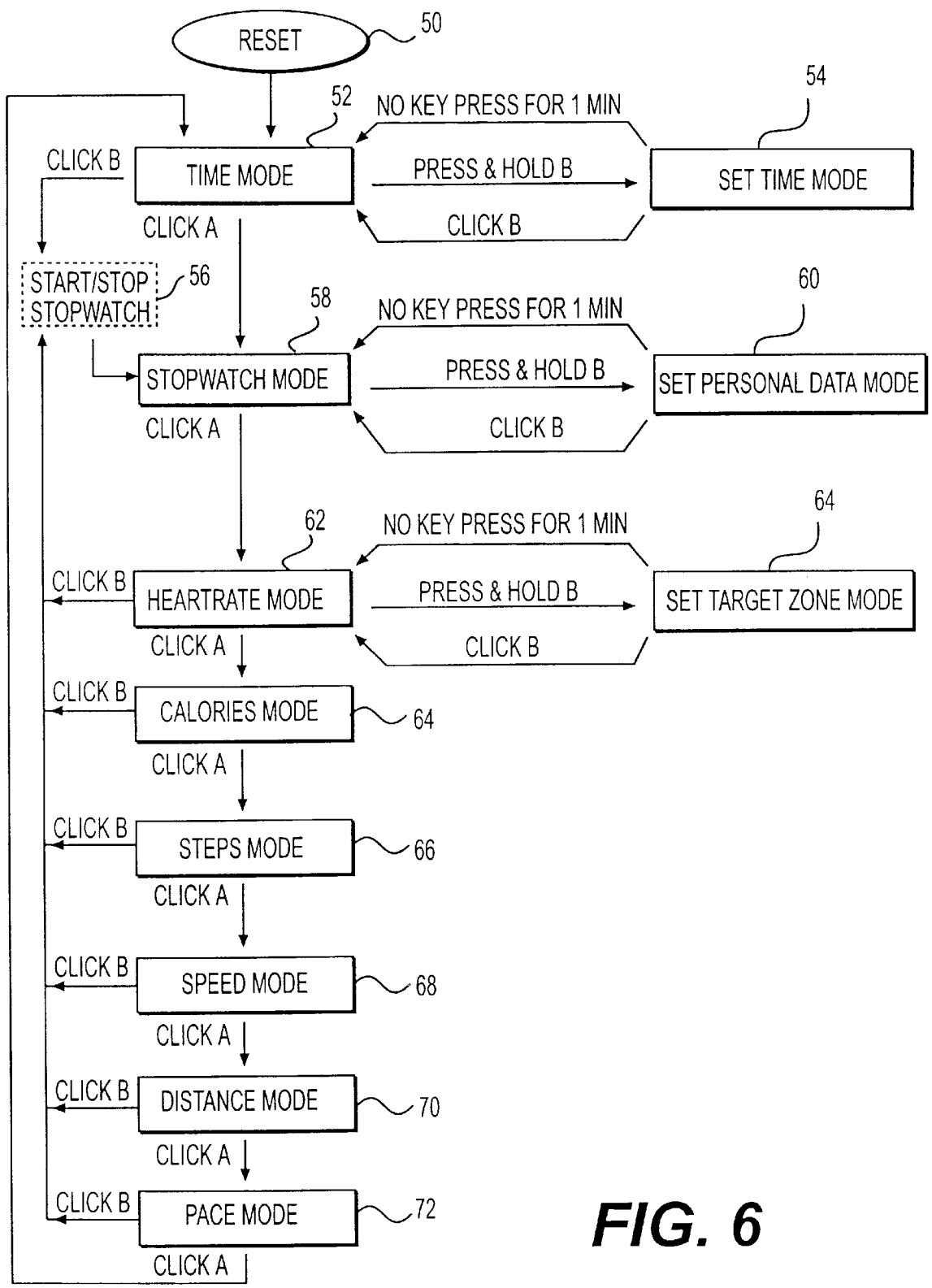
FIG. 6 is a flow chart illustrating the operation of the fitness monitoring device according to the present invention.

Referring to FIG. 6, there is shown a flow chart indicating the operation of the pedometer with the wireless heart rate monitor. A reset button 50 is first activated to reset the fitness monitoring device. Next, the time mode 52 is selected. Within the time mode 52, the user can set 54 the time mode via the operating elements. Next, in the time mode 52, the user can activate the stopwatch 56 and enter the stopwatch mode 58. Within the stopwatch mode 58, the user can set personal data 60 particular to their situation. From the stopwatch mode 58, the user can next enter the heart rate mode 62. During the heart rate mode 62, the user can set a target heart rate zone 64. Also, the user can activate the stopwatch 56 from the heart rate mode 62.

Next, the user can enter the calorie mode 64, the step mode 66, speed mode 68, the distance mode 70, or the pace mode 72 by cycling the mode/reset button. Following the pace mode 72, the fitness monitor device cycles back to the time mode 52. The fitness monitoring device thus provides an electronic pedometer in combination with a wireless heart rate monitor.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A fitness monitoring device, comprising:
    an electronic pedometer which electronically senses a user's body motion at each step;
    a wireless heart rate monitor including a heart rate receiver which wirelessly receives electric signals from a user's heart and outputs a heartbeat signal indicative of an exertion level of said user; and
    an indicator which indicates pedometer functions of the electronic pedometer and heart rate functions of the heart rate monitor.

2. The fitness monitoring device according to claim 1, wherein said indicator is a visual display for displaying the pedometer functions and the heart rate functions.

3. The fitness monitoring device according to claim 2, wherein said electronic pedometer includes a piezoelectric sensor for responding to the user's body motion at each step and providing a pedometer output signal.

4. The fitness monitoring device according to claim 1, further comprising:
    a telemetric transmitter unit for receiving electric signals from a user's heart and wirelessly transmitting said electric signals to the heart rate receiver.

5. The fitness monitoring device according to claim 1, further comprising:
    a single housing in which said heart rate monitor and electronic pedometer are arranged.

6. The fitness monitoring device according to claim 3, further comprising:
    a microprocessor which receives said pedometer output signal and said heart beat signal, said microprocessor including a program to provide visual display data relating to said heart rate and pedometer functions.

7. A fitness monitoring system, comprising:
    a telemetric transmitter unit for receiving electric signals from a user's heart and wirelessly transmitting said electric signals; and
    a fitness monitoring device, comprising:
        (a) an electronic pedometer which electronically senses a user's body motion at each step and outputs a pedometer output signal;
        (b) a wireless heart rate monitor including a heart rate receiver which wirelessly receives the electric signals from the transmitter unit and outputs a heartbeat signal indicative of an exertion level of said user; and
        (c) an indicator which indicates pedometer functions of the electronic pedometer based on the pedometer output signal and heart rate functions based on the heart beat signal from the heart rate monitor.

8. The system according to claim 7, wherein the fitness monitoring device further comprises a microprocessor which receives the pedometer output and heartbeat signals, said microprocessor including a program to provide the pedometer function and the heart beat signal to the indicator.

9. The system according to claim 7, further comprising a single housing in which the fitness monitoring device is arranged.

* * * * *